(12) United States Patent
Castillo et al.

(10) Patent No.: US 7,846,164 B2
(45) Date of Patent: Dec. 7, 2010

(54) PEDICLE PUNCH WITH CANNULA

(75) Inventors: Hector Castillo, Mastic, NY (US);
Stefano Sinicropi, Wordbery, NY (US);
Larry Astwood, Mahwah, NJ (US)

(73) Assignee: Ortho Impact Corporation, Bronx, NY (US)

( * ) Notice: Subject to any disclaimer, the term of this patent is extended or adjusted under 35 U.S.C. 154(b) by 566 days.

(21) Appl. No.: 11/503,860

(22) Filed: Aug. 14, 2006

(65) Prior Publication Data
US 2008/0071302 A1 Mar. 20, 2008

Related U.S. Application Data

(63) Continuation-in-part of application No. 11/156,100, filed on Jun. 18, 2005.

(51) Int. Cl.
*A61B 17/00* (2006.01)
*A61B 17/34* (2006.01)
*A61B 17/88* (2006.01)

(52) U.S. Cl. .................. 606/79; 606/86 R; 606/95; 606/184; 606/297

(58) Field of Classification Search ............ 606/79, 606/86 R, 95, 131, 132, 184, 279, 281, 286, 606/297, 323, 331
See application file for complete search history.

(56) References Cited

U.S. PATENT DOCUMENTS

| 5,464,427 | A | * | 11/1995 | Curtis et al. ............ 606/232 |
| 5,797,909 | A | * | 8/1998 | Michelson ............ 606/914 |
| 5,824,042 | A | * | 10/1998 | Lombardi et al. ....... 623/1.13 |
| 6,371,959 | B1 | * | 4/2002 | Trice ................. 606/97 |
| 2004/0181231 | A1 | * | 9/2004 | Emstad et al. ........... 606/86 |
| 2005/0145940 | A1 | * | 7/2005 | Maeda et al. ........... 257/347 |
| 2005/0192575 | A1 | * | 9/2005 | Pacheco ............... 606/61 |
| 2005/0245940 | A1 | * | 11/2005 | Brock ................ 606/99 |
| 2006/0200123 | A1 | * | 9/2006 | Ryan ................. 606/48 |
| 2006/0271058 | A1 | * | 11/2006 | Ashton et al. ........... 606/96 |
| 2007/0005072 | A1 | * | 1/2007 | Castillo et al. ........... 606/79 |

* cited by examiner

*Primary Examiner*—Thomas C Barrett
*Assistant Examiner*—Sameh Boles
(74) *Attorney, Agent, or Firm*—Thomas A. O'Rourke; Bodner & O'Rourke, LLP

(57) ABSTRACT

The present invention relates to pedicle implements, in particular pedicle implants that involve screws. The present invention includes a handle, a pointy tip, a shaft, a cannula located therethrough and mini protrusions used to prevent toggling. The crux of the present invention is the ability of the user to create an accurate pilot hole via the pointy tip. In addition, the present invention allows the user the ability to insert a pedicle probe through the cannula out through the pointy tip. This allows the user to perform the cannulation portion of the procedure without the use of any thrombatic agents.

22 Claims, 6 Drawing Sheets

PEDICLE PUNCH WITH CANNULA

The present application is a continuation-in-part of previously filed U.S. patent application Ser. No. 11/156,100 filed Jun. 18, 2205, all disclosures of which are hereby incorporated by reference.

FIELD OF INVENTION

The present invention relates to an improved pedicle punch, in particular a pedicle punch that facilitates in the cannulation process during vertebral column surgery.

BACKGROUND OF THE INVENTION

Pedicle screw instrumentation is common in the lumbar spine and is gaining acceptance in the thoracic spine. The use of pedicle screw instrumentation in the spine has evolved over the last two decades. The initial use of pedicle screws began in the lumbar spine. As surgeons have become more comfortable with the complex anatomy required for accurate screw placement, the use of pedicle instrumentation has evolved to include their use in the thoracolumbar and thoracic spine. The impetus behind their increased use is a result of the many advantages that pedicle screw anchorage offers over traditional hook and rod constructs. Improved deformity correction and overall construct rigidity are two important advantages of pedicle screw instrumentation due its three-column control over the spinal elements. First, pedicle screw instrumentation obviates the need to place instrumentation within the spinal canal with its inherent risk of neurologic injury. Second, the placement of pedicle screws is independent of facet or laminar integrity and thus has been extremely useful in traumatic, neoplastic, and degenerative conditions. The benefit of pedicle screws in the thoracic spine has been tempered by the potential for catastrophic neurological or soft tissue injuries due to the close proximity of these structures. The narrow and inconsistent shape of the thoracic pedicles, especially in spinal deformity, makes their placement technically challenging. As a result, surgeons have employed a number of techniques to ensure the safe and efficacious placement of thoracic pedicle screws. Detailed anatomic landmarks used to determine pedicle location, intraoperative imaging including navigation, and neurophysiological monitoring are some of the techniques currently used by surgeons. The implementation of these techniques and a thorough understanding of the complex three-dimensional anatomy have allowed surgeons to successfully place thoracic and thoracolumbar pedicle screws.

Generally speaking, procedures for navigating the pedicle comprise the following steps: (1) decorticating the entry site using a burr and a high speed drill or a rongeur; (2) using an awl or a burr to penetrate the dorsal cortex of the pedicle and create a starter or pilot hole into the pedicle; (3) using a curved or straight pedicle probe to develop a path for the screw through the cancellous bone of the pedicle into the vertebral body (the process hereinafter referred to as "cannulation"). The advancement of the probe must be smooth and consistent and a sudden plunge suggests breaking out of the pedicle laterally. Furthermore, an increase in resistance indicates abutment against the pedicle or the vertebral body; (4) after cannulation, placing the pedicle sounding probe into the pedicle and then palpating the pedicle from within to make sure there is not a medial, lateral, rostral or caudal disruption in the cortex of the pedicle. Sound should also be used to determine that there is bone at the bottom of the pilot hole verifying that penetration of the ventral cortex of the vertebral body has not occurred; (5) after the pedicles have been probed, placing Steinman pins or K-wires bilaterally or unilaterally into the pedicles to confirm the trajectory and entry site, tapping the pedicle screw path if non-self tapping screws are used, and placing the permanent screws with the longest diameter that will not fracture the pedicle. The length of the screw can be determined by measuring the length of the Steinman pin/Kwire/pedicle probe from the pedicle entry site to a depth of 50-80% of the vertebral body; and (6) after pedicle screw placement, decorticating the transverse process and the lateral aspects of the facet joints, connecting the screw to a longitudinal construct, usually a rod or a plate, securing the screws, and placing bone graft on the previously fusion bed. During the entire process the advancement of the probe, the placement of the K-wires, and the ultimate advancement of the pedicle screws is monitored continuously via X-ray exposure or fluoroscopy. The present invention, as mentioned above, relates to cannulation during the pedicle screw procedure. One will now discuss in more detail the present invention, in particular, a pedicle punch that facilitates cannulation during pedicle screw implants.

In general a cannula is a flexible tube, which when inserted into the body may be used to withdraw fluid, insert medication or as in the present invention allow Lenke gearshifts, endoscopic probes, and the like to be inserted into the pedicle. Cannulae normally come with a trocar (a sharp pointed needle) attached which allows puncture of the body to get into the intended space.

Before the cannulation process begins, a posterior cortical breach first must be established on the pedicle, usually via any of the different methods as discussed in applicant's previous filed patent application, such as the burring method, the burning method or the punch method. A number of surgical instruments have been implemented to successfully cannulate thoracic pedicles. The two most common instruments include a gearshift device probe and a cervical curette. Another device that has been implemented with pedicle cannulation is Safe Path, a blunt-tipped, nonaggressive drill that seeks the cancellous portion of the pedicle. The pedicle punch of the present invention may be used with any of the aforementioned devices.

One will now discuss the utility of the present invention, for illustrative purposes one will discuss the present invention when used with a Lenke gearshift. A curved Lenke gearshift or a straight curette (3-0 cervical) may be used to probe or mature the intended screw path within the pedicle. The gearshift may be inserted via the cannula of the present invention. Once the neurocentral junction of the pedicle is reached (typically at a depth of 20 mm) the gearshift is removed and reinserted with the curved tip facing away from the surgeon. Positioning the pedicle probe tip medially assists in guiding the probe medially within the vertebral body. Next, the pedicle tract is palpated with a ball-tipped probe to verify the presence of a bony floor and an intact four-wall boundary. If a violation of bony integrity is noted at this point, redirecting the gearshift may be necessary in order to assure safe screw placement. The pedicle path is then tapped (preferably undertapped by 0.5-1.0 mm compared to the diameter of the selected screw) and the tract is repalpated with the ball-tipped probe to detect for any bony breaches. The pedicle screw is now inserted. Following screw insertion, intraoperative imaging is then performed to verify acceptable screw positioning. Triggered EMG testing may be used to evaluate for proper lower thoracic screw placement (T8-T12), while motor-evoked potential (MEP) monitoring assists in monitoring spinal cord function for all thoracic levels instrumented. Once all screws are placed and the applicable screws have been tested via triggered EMG the rod can be docked to complete the construct.

Even though most pedicle implant procedures are successful there is need for improvement. That is, after a posterior cortical breach is established, via the burring method or the burning method, the surgeon would first have to arrest the bleeding associated with these pedicle screw implant methods, before inserting one of the aforementioned probes.

Another drawback of the pedicle screw implant procedure is that the patient, surgeon, and medical staff are exposed to deleterious amounts of radiation, more specifically those deleterious amounts of radiation associated with fluoroscopy during the pedicle screw implant procedure. One way surgeons can protect themselves is with eyewear, thyroid shields, and lead aprons. However, studies with cadavers have shown that the surgeon's hands are still at a high risk of radiation exposure. In one study average fluoroscopy exposure time was 9.3 s per screw. and the average hand dose rate was 58.2 mrem/min. The internationally recommended maximum limit for annual hand radiation exposure is 50,000 mrem. In the same study a significant increase in hand dose rate was noted when placement of the screw was on the same side of the beam source as well as when a heavier cadaver was imaged.

Thoracic and thoracolumbar pedicle screw instrumentation is proving to be a safe and reliable method of obtaining rigid segmental fixation of the thoracic spine. A thorough understanding of the complex 3D spinal anatomy is required to safely place this type of instrumentation. The biomechanical benefits that are derived from using pedicle screw instrumentation in all forms of spinal pathology are the driving force behind more and more surgeons incorporating thoracic and thoracolumbar pedicle screw placement into their practices. Surgeons however, must be well versed in the placement of complex spinal instrumentation in order to accurately and safely use this method of instrumentation in all types of spinal disorders. The present invention, because of its unique design aids surgeons in the pedicle cannulation step via a pedicle punch that incorporates a cannula.

OBJECTS OF INVENTION

It is therefore an object of the present invention to provide a method and apparatus for use in spinal implant procedures, which is cost effective to produce and easy to manufacture.

It is another object of the present invention to provide an apparatus for spinal implant procedures that is easy to use.

It is therefore an object of the present invention to provide an apparatus for use in spinal implant procedures wherein the penetration of the pedicle with a probe and subsequent insertion of the pedicle screw is accomplished quickly, accurately, flawlessly and without breaking out of the pedicle path.

It is an even further object of the present invention to provide an apparatus for use in spinal implant procedures that will significantly reduce the exposure of both the surgical team and the patient to radiation exposure and more particularly to fluoroscopic radiation exposure.

It is a further object of the present invention to provide an apparatus for use in spinal implant procedures in which the starter hole or pilot hole has a trajectory path whose vector is in complete alignment with the pedicle axis right from the very beginning of the pedicle penetration process.

Another object of the present invention is to provide an apparatus that allows the surgeon to know the exact starting point of the pedicle, without any guessing, and create such starting point without burring.

Yet another object of the present invention is to provide an apparatus for use in spinal implant procedures which allows two surgeons to conduct the instrumentation on the patient's spine at the same time, thereby dramatically reducing the time normally associated therewith.

It is still another object of the present invention to provide an apparatus for use in spinal implant procedures which allows the surgeon to create a posterior cortical breach on the pedicle and insert a pedicle probe in one step.

SUMMARY OF INVENTION

In the present invention the pedicle punch includes a cannula, which allows the surgeon to probe the pedicle without removing the pedicle punch.

The pedicle punch of the present invention is designed to be easily located against a vertebra pedicle in a proper position. The pedicle punch is designed to be readily positioned in complete alignment with the centrally located pedicle axis of the vertebra pedicle through minimal use of imaging technology. Once properly positioned the punch may be deployed into the vertebrae pedicle quickly and effectively to create a pilot hole having (i) a diameter wide enough to accommodate instrumentation, for example, a probe or the like. In addition, the punch provides a trajectory path vector that is totally aligned with the pedicle axis of the vertebrae pedicle.

The pedicle punch is preferably formed from at least two different materials. The first is a radiation translucent material and the second, a radiation opaque material. The pedicle punch comprises, in general, a proximal end, a distal end, a composite shaft, joining the two ends. The proximal end can have any shape that is ergonomically designed to provide a driving surface for the pedicle punch. The proximal end provides a driving surface for forcing the pedicle punch into the vertebrae pedicle. This surface must be made of a material that will not shear or break, causing a portion of the punch to become separate from the remainder of the punch. Separation of a portion of the pedicle during treatment could contaminate the site where the treatment is occurring, causing infection, a puncture, etc. The composite shaft is attached to and projects from the proximal end and terminates to a sharp conical spike or pointy tip. The composite shaft has a radiation opaque central core running transversely though it's entire length and a radiation translucent outer covering or layer surrounding at least a portion of the central core. The radiation opaque center core extends beyond the radiation translucent outer layer to form the bottom section having a sharp point or pointy tip of the shaft. The outer coating or cover may have an outwardly protruding lip that is located on the composite shaft adjacent to the sharp conical spike or pointy tip, right on the widest diameter thereof and preferably concentric thereto.

In addition, the pedicle punch of the present invention includes a cannula, preferably centrally located, which allows a pedicle probe to be inserted to facilitate cannulation. The addition of the cannula in the present invention improves on the relevant and material prior art. For example, the unique design of the pedicle punch allows the surgeon to leave it attached to the pedicle being operated on, which allows the surgeon to insert the pedicle probe into the pedicle without the need for any thrombotic agents, because the lip of the pedicle punch prevents blood flow out of the pilot hole. Whereas in the prior art the burring of starting or pilot holes can cause significant bleeding thereby requiring the administration of thrombotic agents to stop the blood flow before the insertion of the probe. In addition, since the pedicle punch of the present invention is not removed the surgeons can use it as a guide, thus reducing exposure of the surgeon's hands to the harmful trace amounts of radiation.

BRIEF DESCRIPTION OF INVENTION

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring more specifically to the drawings, FIGS. 1-4 generally depicts a pedicle punch at 10. The pedicle punch 10 is designed to replace currently available technology and tools currently being used to create pilot holes in pedicle vertebrae during spinal fusion surgical procedures including awls, drills, etc., and more particular during the pedicle screw insertion process. The pedicle punch has been engineered to be readily positioned against the vertebrae pedicle, in the desired alignment with the centrally located pedicle axis through minimal use of imaging technology, such as for example x-rays, fluoroscopy, virtual fluoroscopy, etc., and once properly positioned to be deployed into the vertebrae pedicle quickly and effectively.

Figure 5:
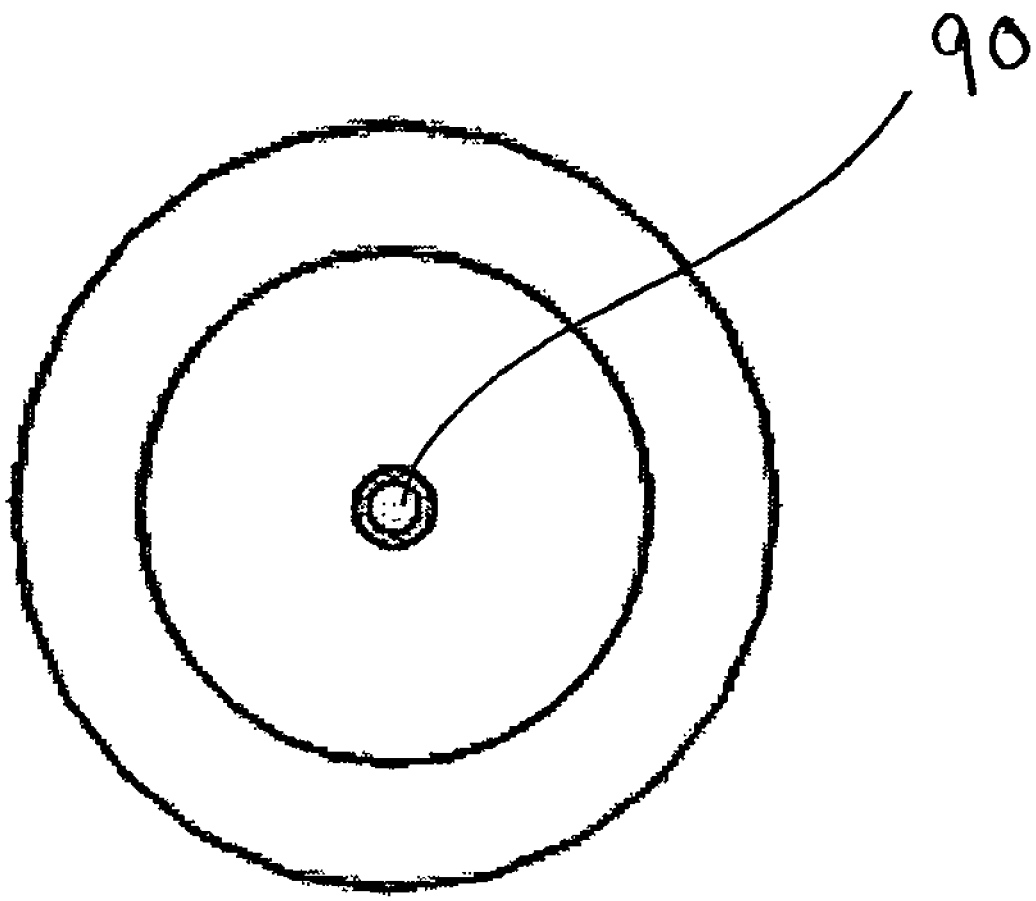
FIG. 5 is a top view of the bulls eye left after the pedicle punch of the present invention has been tapped.

Once deployed into the pedicle, pedicle punch 10 remains in position on the vertebrae pedicle until such time as the surgeons remove it to proceed to the next instrumentation step in the pedicle screw insertion process. When removed, the pedicle punch 10 leaves behind, on the vertebrae pedicle, a starter hole, also known as a pilot hole (hereinafter "a pilot hole") 90, as seen in FIG. 5, having a diameter of preferably 3-4 mm wide and a trajectory path vector that is totally aligned with the pedicle axis of the vertebrae pedicle. In many instances, the pedicle punch provides for almost a perfect pilot hole without undue difficulty. Thus, the surgeons will not have to engage in any further burring, or hole making, or checking with K-wires to determine whether in fact they have correctly identified the central pedicle axis of the pedicle vertebrae before proceeding to the next step. Accordingly, not only will the inventive pedicle punch 10 help create the desired pilot hole, but it will allow the surgeon to reduce a significant amount of time from the pedicle screw insertion process, as well as reduce a significant amount of deleterious radiation to which the surgical team and the patient are exposed to, and minimize the amount of bleeding during the procedure.

The pedicle punch 10 is formed of both radiation translucent and radiation dense material. The radiation translucent material could be any material that allows the radiation of imaging technology used during the pedicle screw insertion processes, to pass right though the material so that the material is not reflected on the viewing screen. Preferred radiation translucent materials include glass, ceramic and plastic materials that will not shatter when subjected to a driving force from e.g., a hammer, punch, etc. Furthermore, the radiation translucent material must also be very strong so that it can sustain the forces used on it during the deployment of the pedicle punch 10 into the vertebrae pedicle without cracking, shearing, splintering, etc. In the preferred embodiment of the pedicle punch 10 the radiation translucent material used is a plastic material such as polyester or nylon based material or blends thereof. Suitable plastic materials include polyester methyl ketone (PMK), Kevlar, polycarbonate, glass filled nylon and polypropylene. The material should be chosen not only for its ability to allow radiation through and its strength, but also for the low manufacturing costs associated therewith. The overall length of the pedicle punch 10 will be commensurate with the application.

Referring once again to FIG. 1, the pedicle punch 10 comprises a proximal end, or head 20, a distal end 40 and a composite shaft or body 30 connecting the two ends. The overall shape of the punch can vary based on a number of factors, such as, the desired thickness, the overall length, the shape of the head which receives a driving force, the shape of the body which facilitates handling, etc. In a preferred embodiment there may be an outwardly protruding lip, or base 50 extending from a skirt portion 80 of body 30, as seen in FIGS. 1-4 Although the drawings show a generally circular cross section for the pedicle punch, it will be appreciated that the punch may have any suitable cross section so that it may be easily handled.

During use and deployment, the pedicle punch 10 will be held by its head 20 or along the shaft or body 30. Thus, the head 20 can be bulbous or any disk shaped, or knob shaped, mushroom shaped etc. or any shape for that matter that provides a head for receiving a driving means that forces the pedicle punch into the pedicle. Preferably, the shape is ergonomically designed to act as the handle of the pedicle punch 10. The head 20 may have a waist 20a, which may be defined by proximal side 22 and a distal side 24 where the proximal side can have a different cross section than the composite shaft 30.

Figure 1:
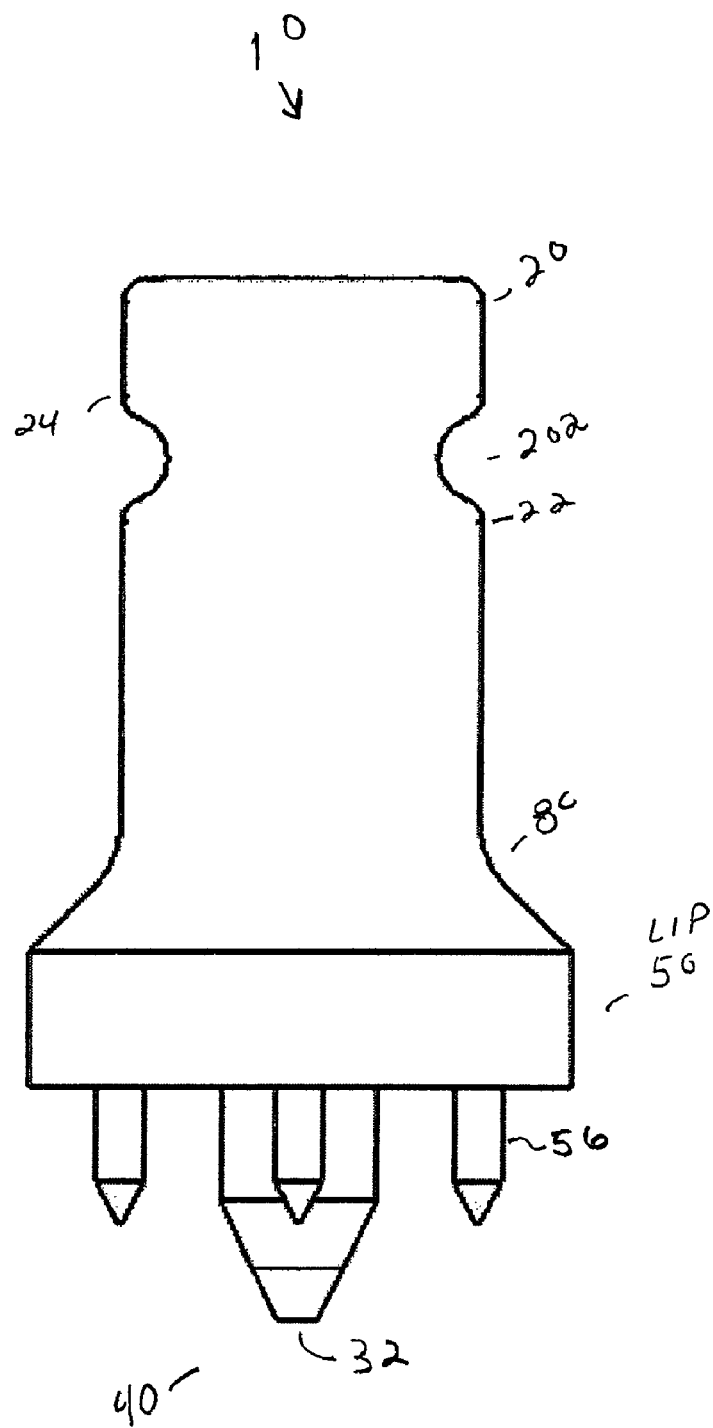
FIG. 1 is a perspective view of the pedicle punch of the present invention.
Figure 2:
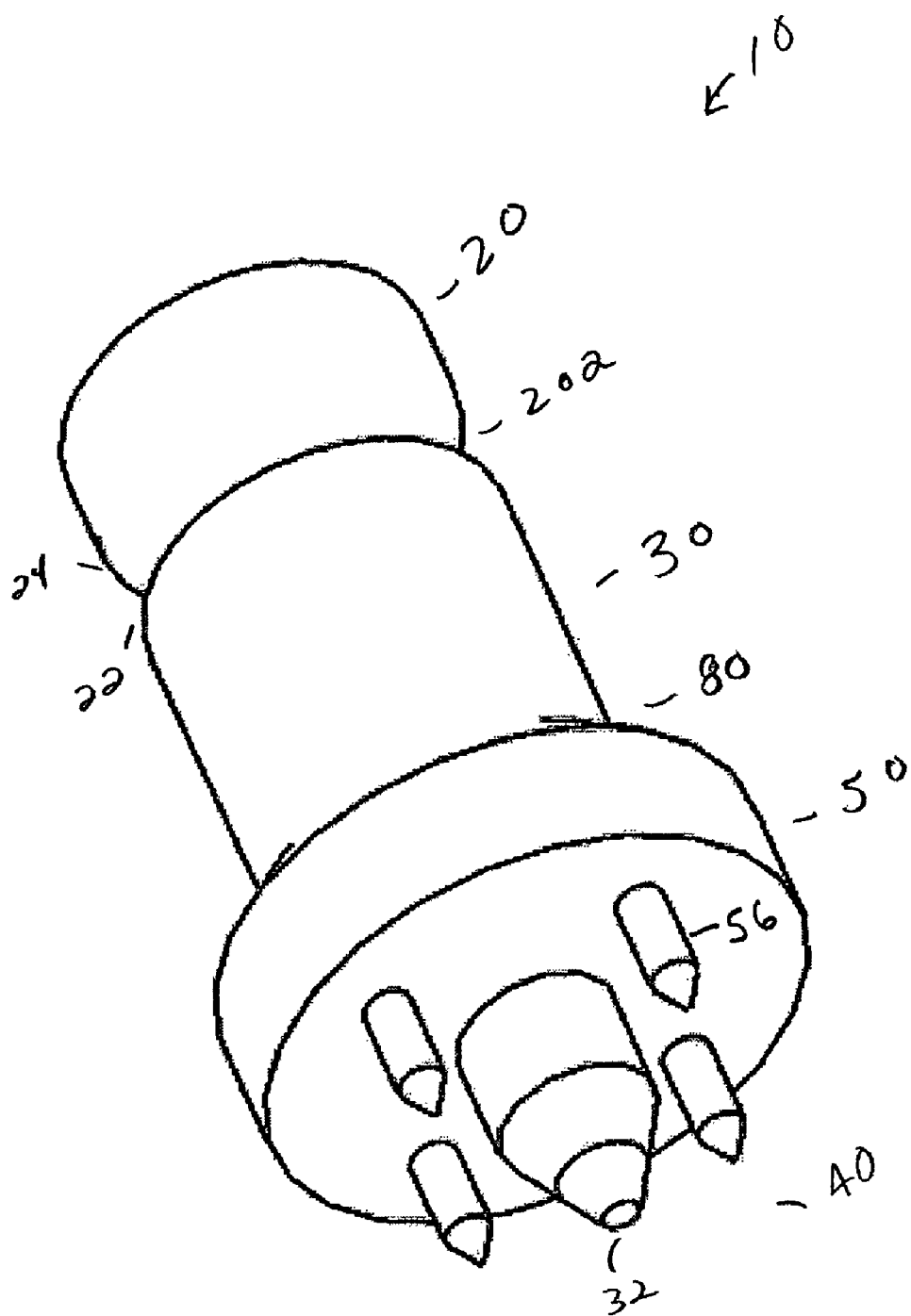
FIG. 2 is a side view of the pedicle punch of the present invention.
Figure 3:
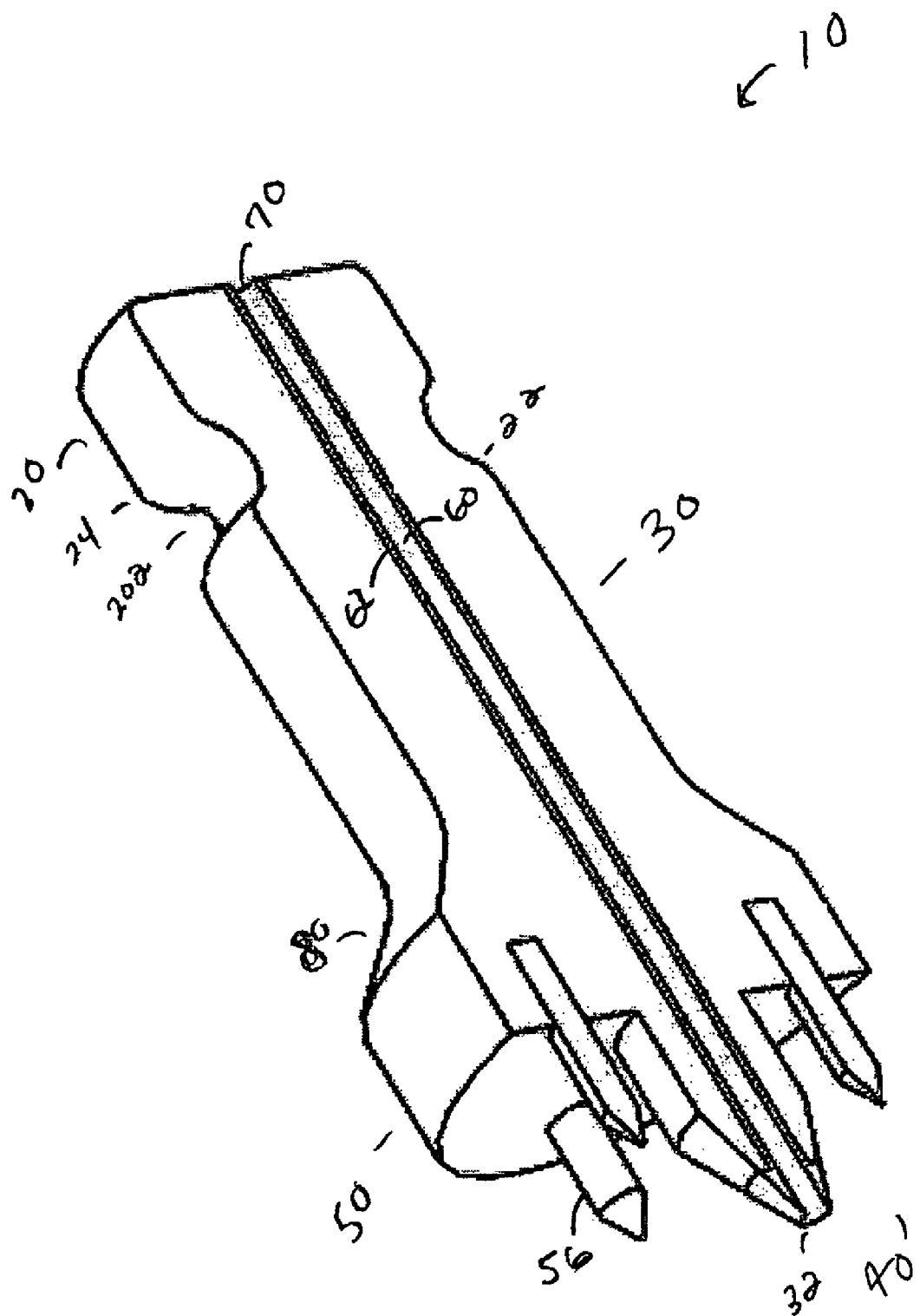
FIG. 3 is a cut out view of the pedicle punch of the present invention.
Figure 4:
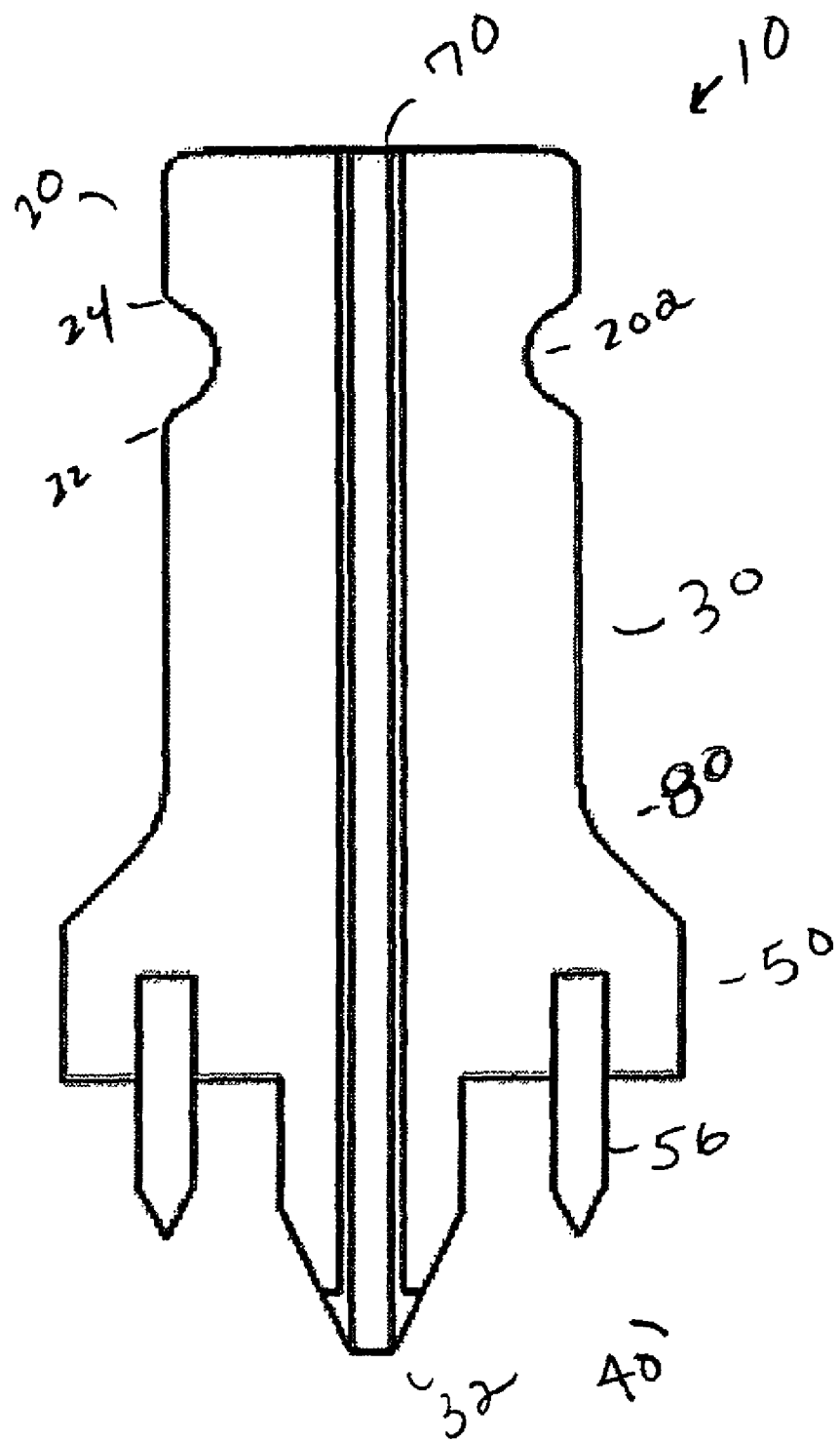
FIG. 4 is a side view of the pedicle punch of the present invention with emphasis being focused on the cannula.

In the embodiment shown in FIGS. 1-4 the composite shaft or body 30 is attached to and projects from generally the center of the proximal side 22 of head 20 of the pedicle punch 10 and ends in a sharp preferably conical spike or pointy tip 32 at the distal end 40 of the pedicle punch 10. Body 30 may be defined as having a skirt portion 80 and a base or lip portion 50. It will be appreciated that the tip need not be conical as long as it is sharp and can pierce the surface of the pedicle. The body 30 comprises a radiation opaque or radiation dense center core 60 (hereinafter "the center core 60") and a radiation translucent outer layer 62 encasing the center core 60. Where the cross section of the body 30 is circular the translucent outer layer is preferably concentric to the center core 60. Where other configurations are used for the cross section, the center core 60 is preferably in the center of the composite shaft 30. Under imaging technology the composite shaft is radiation translucent on the outer layer 62 and radiation dense, or radiation opaque, in its center core 60, thereby appearing on the screen as a single round dot. The center core 60 runs transversely, preferably along the entire length of the pedicle punch. In another embodiment, it runs the length from the center of the distal end 24 at the proximal end 20, to the very tip of the distal end 40, extending sufficiently beyond the distal edge of the outer layer 62 to form the bottom half of the sharp conical point or pointy tip 32 of the shaft 30, at the distal end 40 of the pedicle punch 10. The distal end 40 of the pedicle punch 10 can be generally perpendicular to the center axis that extends from one end of the center core to the sharp tip. In another embodiment, the distal end 40 may be recessed or may be conical in shape with the sharp tip extending from the conical portion of the distal end. As shown in FIG. 3, the distal end may be in the form of a flat ring having a raised center portion. The present invention allows the surgeon to insert the pedicle probe into the pedicle without the need for any thrombotic agents, because the lip of the pedicle punch prevents blood flow out of the pilot hole. The center portion is preferably made from the same material as the outer layer 62. The conical portion of the outer layer may have a first section, having a side wall and generally in the shape of a dish or ring with an open center. On top of the ring there is a truncated conical section of the outer layer 62 also having an open center. The open center is for receiving the radiation opaque center core 60.

It is the radiation dense or radiation opaque center core 60 that allows the pedicle punch 10 to be placed concentrically with the vertebrae pedicle and in perfect alignment with the pedicle axis, and to ultimately create a pilot hole on the vertebrae pedicle that also has a trajectory path vector in direct alignment with the pedicle axis. This alignment can be assisted by the presence of additional radiation dense pins that form a bull's eyed configuration when seen under radiation. These pins 56 extend from the distal end of the punch as shown in FIG. 3. These pins are made of a radiation dense material as is the central core.

In the preferred embodiment, metal is used to form the radiation opaque or radiation dense center core 60. Metal imparts great strength to the bottom end of the sharp conical spike or pointy tip 32 of the distal end 40 of the pedicle punch 10 and to the entire composite shaft 30. Such strength renders the pedicle punch 10 capable of not only creating the pilot hole, as defined above, when deployed on the vertebrae pedicle, but of also sustaining the forces necessary to create the pilot hole without chipping, disintegrating, or otherwise compromising the integrity of the pedicle punch 10. Any metal that is radiation opaque can be used for the dense center core 60. A preferred metal is one having a Durometer hardness of 40 and up. The metal is preferably a casehardened metal. One preferred radiation opaque material is stainless steel. By the term radiation opaque and radiation translucent is meant a material when used in the core 60 will give a radiation fingerprint different from the material used in the cover or coating, so that the location where the sharp tip of the pedicle punch is can be ascertained under radiation.

The specifications for the diameter of the entire sharp conical spike or pointy tip 32 comprising partly radiation translucent and partly radiation opaque material, from its widest point and tapering distally to form the pointy tip, will range so that when the pedicle punch 10 is deployed in the pedicle and thereafter removed therefrom, it leaves behind a pilot hole having dimension of 3-4 mm. Obviously, if a larger pilot hole is desired then the diameter will be changed analogously. However, the smallest diameter at the most distal pointy tip end should preferably be no greater than about 0.25 mm, for maximum penetrating power.

The outwardly protruding base 50 is located on the shaft 30, adjacent to the sharp conical spike or pointy tip 32, and where the widest diameter of the sharp conical spike or pointy tip 32 begins, and concentric thereto. It has a proximal side 52 and a distal side 54. The distal side 54 of the outwardly protruding lip 50 is provided with at least three teeth, knobs or mini protrusions 56 to prevent toggling of the pedicle punch 10, once it is deployed in the vertebrae pedicle.

The pins that surround the center core are secured to the outer layer by any suitable means. Preferably, the pins are embedded in the outer layer so that they will not break off during use. The purpose of the pins is to provide a "bull's eye" or "cross hairs" arrangement of the sharp tip at the center so that when radiation is applied, the site where the pedicle punch is inserted is illuminated to facilitate insertion in the proper position, as well as aid in determining whether the pedicle is in the proper position. The pins also help to secure the pin in position after the punch has been inserted into the pedicle. Although four pins are depicted in the Figure, it will be appreciated that two or more pins, preferably three or more pins, will accomplish the desired bull's eye arrangement. In another embodiment, the pins may be replaced with a raised ring of a radiation opaque material. This raised ring forms the outer ring of the bull's eye and preferably has a sharpened outer surface.

The pedicle punch of the present invention may be formed by any suitable means. One method is by extruding the outer covering about the center core 60. Another method of forming the punch is by a casting method such as die casting.

Figure 6:
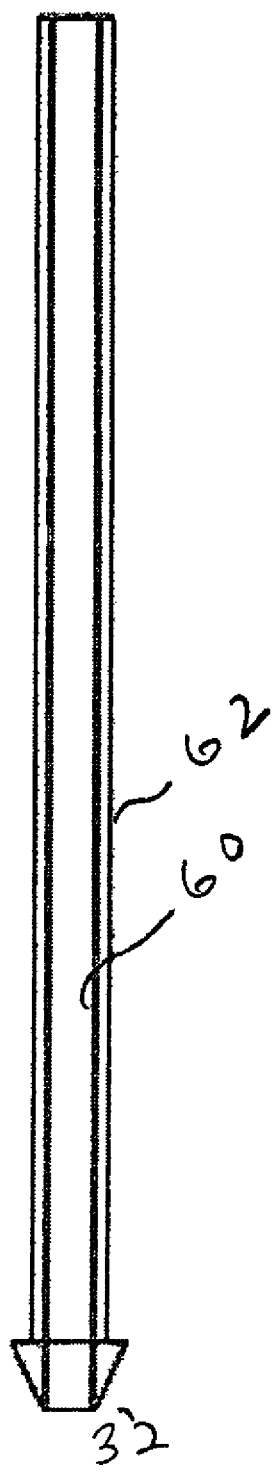
FIG. 6 is a side view of the cannula implemented in the pedicle punch of the present invention.

Turning one's attention to FIGS. 3 and 6, one can see cannula 70 of pedicle punch 10 of the present invention. Cannula 70 may be a generally cylindrical in shape, which may extend from head 20 to the proximal pointy tip 32 of base 50. It will be appreciated by those skilled in the art that cannula 70 will be sized and shaped so as to be able to receive all pedicle probes in the known art. Cannula 70 may be constructed from any suitable material known in the art, such as plastics, plastic materials include polyester methyl ketone (PMK), Kevlar, polycarbonate, glass filled nylon and polypropylene. The material should be chosen not only for its ability to allow radiation through and its strength, but also for the low manufacturing costs associated therewith. Cannula 70 has inner surface 71a and outer surface 71b. In one embodiment outer surface 71b may be in contact with inner core 60, or in a preferred embodiment outer surface 71b may not be in contact with inner core 60. With the latter embodiment an insulation layer may be utilized. In normal operation, after the posterior cortical breach has been performed by the surgeon. The surgeon will then insert the appropriate pedicle probe. For example, a surgeon may implement the Lenke gearshift to perform the initial cannulation process, thus after the pilot hole is created the surgeon may then feed the pedicle probe through the cannula portion of the pedicle punch.

The thickness of the outwardly protruding base 50 is not critical so long as it does not interfere with the proper location of the pedicle punch. However, it can generally range anywhere from 1-2 mm in thickness. Once the pedicle punch is deployed into the pedicle, the outwardly protruding base 50 comes in direct contact with the pedicle and effectively seals any wound that is created by the pedicle punch as it is being deployed thereby imparting a hemostatic characteristic to the pedicle punch 10, as well. Consequently, the presence of the outwardly protruding base 50 in combination with the fact that the punch is left in the wound, minimizes bleeding tremendously and eliminates the use of thrombotic agents to stop the blood flow. Since excessive bleeding is no longer a critical problem, the present process might be expanded to be used with patients normally not recommended for spinal fusion surgery due to their inability to properly clot.

The method for using the inventive pedicle punch 10 described above, comprises the following steps: (a) using an image generating apparatus, such a fluoroscope, to accurately map the pedicle and the axis thereof. The pedicle will be depicted as a circle on the apparatus screen, with the center point of the circle corresponding to the central axis of the pedicle; (b) placing the pedicle punch 10 on the vertebrae pedicle just mapped; c) manipulating, moving and positioning the pedicle punch 10 until such time that the radiation translucent central core 60, which will appear as a solid dot on the screen of the image generating apparatus, is located right in the center of the circle corresponding to the pedicle just mapped, concentric to and in complete alignment with the mapped pedicle axis to form a bull's eye (the solid center core 60 dot in the center and the pedicle circle concentrically aligned around said dot); (d) once the bull's eye is achieved on the screen of the image generating apparatus, deploying the pedicle punch 10 into the mapped vertebrae pedicle using an appropriate force generating tool such as a surgical mallet; and (e) confirming the exact placement of the pedicle punch with the image making instrument and leaving the pedicle punch in place until needed to be removed. The surgeon is now ready for identification of the next pedicle and its axis and the steps are repeated until all of the pedicle punches are placed at all levels to be instrumented. Upon completion of the placement of the pedicle punches, the surgeon is ready to remove the pedicle punches one by one, and for each perfect pilot hole left behind on the vertebrae pedicle by the pedicle punch, to proceed to the next step of instrumentation in the pedicle screw insertion process.

In an alternate embodiment of the inventive pedicle punch described above, head 20 is provided with a groove for the purpose of providing the surgeon with a better grip on the pedicle punch 10.

In yet another embodiment of the invention described herein above, either the outer perimeter of head 20 or the outer perimeter of the outwardly protruding base 50 is further provided with an opaque material, such that when the central core 60 is "bull's eyed" with the pedicle, the bull's eye comprises a center dot and two outwardly extending concentric circles, as opposed to one circle concentric to the center dot, as described hereinabove.

It is clear then from all of the above, that incorporating the pedicle punch 10 and the method of use thereof into spinal implant procedures and more particular into pedicle screw insertion processes accomplishes all of the invention's objectives as set forth hereinabove. It leads to the penetration of the pedicle with a probe and subsequent insertion of the pedicle screw quickly, accurately, flawlessly and without breaking out of the pedicle path. Its ease of use significantly decreases the surgeons' learning curve, in that it allows the surgeon to know the exact starting point of the pedicle, without any guessing. It practically eliminates dural or neural injury. It dramatically reduces the time normally associated with such procedures not only because it reduces the steps necessary for the creation of the perfect pilot hole, but because it can accommodate two surgeons working at the same time on one patient. Its minimum use of image making instruments and the speed at which the pedicle axis can be mapped and "bull's eyed", dramatically reduces the exposure of both the surgical team and the patient to radiation exposure and more particularly to fluoroscopic radiation exposure.

Its significant reduction of bleeding, partly because the burring of pilot holes is completely eliminated, thereby also eliminating the creation of pilot holes due to mistaken identification of pedicle axes, partly because the pedicle punch is left in the pilot holes until such time as the surgeons are ready, and partly because of the hemostatic effect of the pedicle punch due to its protruding lip, the inventive pedicle punch minimizes the administration of thrombotic agents during the pedicle insertion process. Finally, it unequivocally creates the perfect pilot hole, i.e., a pilot hole having (a) a diameter that is sized perfectly to accept the next instrument; and (b) a trajectory path vector in complete alignment with the pedicle axis right from the very beginning of the pedicle penetration process. Thus, the surgeon saves even more time, since he does not have to correct the initial vector of the trajectory path of the pilot hole nor compensate for any errors or deviations thereof from the pedicle axis.

As various changes could be made in the above constructions without departing from the scope of the invention, it is intended that all matter contained in the above description shall be interpreted as illustrative and not in a limiting sense. In the view above it will be seen that several objects of the invention are achieved and other advantageous results attained, as defined by the scope of the following claims.

What is claimed is:

1. A hemostatic pedicle punch for establishing a hole in a vertebra pedicle when deployed thereon during pedicle screw insertion processes, said hemostatic punch comprising:
   a shaft, said shaft having a length formed by a proximal end and a distal end; said shaft flaring outwardly between said proximal end and said distal end to form an annular lip at said distal end;
   a truncated spike, said truncated spike projecting from said distal end of said shaft;
   said hemostatic pedicle punch being formed of a radiation translucent material except for a radiation opaque center core, said radiation opaque center core running longitudinally along at least part of said length of said pedicle punch, beginning from said proximal end
   an orifice running through said hemostatic pedicle punch, said orifice beginning at said proximal end of said shaft and running through said central core to said truncated spike;
   two or more mini-protrusions protruding from said distal end and terminating in a sharp point, said two or more mini-protrusions working in combination with said lip to stabilize said pedicle punch to provide hemostatic penetration of said pedicle; and
   a cannula, said cannula comprising a plastic tube, said tube having an inner surface and an outer surface, and first and second ends adapted to receive and transport a pedicle probe; said cannula being disposed in said orifice of said pedicle punch until said second end contacts said truncated spike; said cannula second end comprising a truncated conical shape for punching through said pedicle.

2. The hemostatic pedicle punch according to claim 1, wherein said radiation translucent material is selected from the group of radiation translucent materials consisting of plastics, metals, and ceramics; and wherein said radiation opaque material is metal.

3. The hemostatic pedicle punch according to claim 1, wherein said truncated spike comprises a cylindrical protrusion transitioning to a truncated conical shape, said truncated conical shape having a flat annular end surface; and wherein said truncated conical shape of said cannula comprises a flat annular end surface.

4. The hemostatic pedicle punch according to claim 3 wherein said truncated spike produces a punched hole having a diameter in the range of approximately three to four millimeters.

5. The hemostatic pedicle punch according to claim 1, wherein said two or more mini-protrusions comprise a plurality of mini-protrusions, and wherein said plurality of mini-protrusion are radiation opaque.

6. The hemostatic pedicle punch according to claim 4 wherein said flat annular end surface of said cannula has a diameter of less than 0.25 millimeters to facilitate pedicle penetration.

7. The pedicle punch according to claim 1 wherein said cannula runs the entire length of said pedicle punch.

8. The pedicle punch according to claim 1 said wherein said cannula is generally cylindrical in shape.

9. The pedicle punch according to claim 1 wherein said outer surface of said cannula is in contact with said inner core.

10. The pedicle punch according to claim 1 wherein the outer surface of said cannula is in contact with a layer of insulation, and said insulation is in contact with said inner core.

11. A method for hemostatically creating a posterior cortical breach, said method comprising the steps of:
   (a) accurately mapping the perimeter of the a vertebrae pedicle and the axis thereof;
   (b) placing a pedicle punch on said mapped pedicle, said pedicle punch comprising a pedicle punch according to claim 1
   (c) moving and positioning said pedicle punch until said radiation opaque center core appears as a central dot upon application of imaging technology, and wherein said central dot is aligned with said axis of said mapped pedicle;
   (d) deploying said pedicle punch into said mapped vertebrae pedicle using an appropriate force to form a cylindrical breach having a diameter wide enough to accommodate the instrumentation of a pedicle screw insertion process, and said cylindrical breach having a trajectory path vector that is as closely aligned to said mapped pedicle axis as possible
   (e) insertion of a pedicle probe into said breached pedicle through said cannula of said hemostatic pedicle punch to examine said breached pedicle; said annular lip of said pedicle punch contacting said perimeter of said pedicle to seal said breach and prevent bleeding therefrom until subsequent removal of said pedicle punch; said two or more mini-protrusions of said pedicle punch and said annular lip serving to prevent toggling of said pedicle punch to thereby maintain said sealing of said breach.

12. The method for hemostatically creating a posterior cortical breach according to claim 11, wherein said two or more mini-protrusions of said pedicle punch comprise a plurality of radiation opaque mini-protrusions, said plurality of radiation opaque mini-protrusions forming a bulls-eye target upon said application of imaging technology to further aid in alignment of said radiation opaque core of said pedicle punch with said pedicle axis.

13. A hemostatic pedicle punch for creating a hole in vertebra pedicles to accommodate pedicle screw placement required for spinal instrumentation installation processes, said hemostatic pedicle punch comprising: a cylindrical shaft, said shaft having a length defined by a first end and a second end, said cylindrical shape being defined by a generally constant diameter about an axis; said shaft flaring outwardly at a position between said first end and said second end to form a cylindrical base shaft region at said first end and having a base shaft diameter greater than said shaft diameter, said first end of said base shaft comprising a generally flat surface, said generally flat surface being orthogonal to said cylinder axis; a central protrusion protruding from said generally flat surface at said first end, said central protrusion beginning at said first end of said shaft as a cylindrical protrusion with a diameter less than said shaft diameter, and being generally concentric to said axis of said shaft, said cylindrical protrusion transitioning abruptly into a conical frustum, said conical frustum terminating in a planar end surface; said central protrusion having a length defined by a distance between said planar end surface of said frustum and said flat surface of said first end of said base shaft; an orifice through said pedicle punch, said orifice having an axis approximately concentric with said shaft axis, said orifice beginning at said second end of said shaft and through said pedicle punch to said planar end surface of said frustum of said central protrusion; two or more peripheral protrusions, said two or more peripheral protrusions protruding orthogonally from said generally flat surface at said first end; each of said two or more protrusions beginning at said first end of said shaft as a cylindrical protrusion and transitioning abruptly into a conical shape that terminates in a sharp point; each of said two or more peripheral protrusions being located equidistant from respective peripheral protrusions and with each having an axis beginning on said generally flat surface and at the same radial distance from said shaft axis; each of said peripheral protrusions having a common length defined by a distance between said sharp point of said conical shape and said flat surface of said first end of said base shaft, and also having a diameter being less than said diameter of said central protrusion; said length of said two or more peripheral protrusions being less than said length of said central protrusion but permitting shallow depth pedicle penetration to serve in combination with said base shaft to prevent toggling of said pedicle punch and permit hemostatic pedicle penetration by said central protrusion; said pedicle punch being a composite part formed of two materials with each having distinct properties, a first of said two materials being a radiation translucent material with suitable properties to withstanding impact during punching, and a second material being radiation opaque; said pedicle punch being formed generally of said radiation translucent material but for a cylindrical core being formed of said radiation opaque material, said cylindrical core having an axis concentric with said shaft axis, said cylindrical core comprising at least a portion of said pedicle punch between said second end and said planar end surface of said central protrusion; a cannula, said cannula comprising a tube having a cylindrical outer surface and a cylindrical inner surface, said cylindrical outer surface transitioning into a conical frustum with a base surface protruding outward from said cylindrical outer surface, and an annular end surface; said cannula being fixedly disposed within said orifice of said pedicle punch with said base of said cannula frustum contacting said planar end surface of said conical frustum of said central protrusion.

14. A hemostatic pedicle punch according to claim 13, wherein said two or more peripheral protrusions comprise a plurality of peripheral protrusions, and wherein said plurality of protrusions are formed of said radiation opaque material to create a bulls-eye radiographic image in combination with said radiation opaque core to assist in locating said pedicle punch prior to punching.

15. A hemostatic pedicle punch according to claim 14, wherein said plurality of peripheral protrusions are interconnected and form a continuous ring shape.

16. A hemostatic pedicle punch according to claim 14, wherein said radiation opaque plurality of peripheral protrusions are integrally formed with said radiation translucent base shaft.

17. A hemostatic pedicle punch according to claim 14, wherein said radiation opaque plurality of peripheral protrusions are embedded into said base shaft.

18. A hemostatic pedicle punch according to claim 14, wherein an insulation layer separates said core and said cannula.

19. A hemostatic pedicle punch according to claim 14, wherein said annular surface of said cannula has a diameter less than 0.25 millimeters to facilitate penetration by said hemostatic pedicle punch; and wherein said hole punched in said pedicle has a diameter in the range of approximately three to four millimeters.

20. A method of efficient vertebrae pedicle screw placement required for installation of instrumentation in spinal implant procedures, wherein said efficient method minimizes administration of thrombotic agents to reduce bleeding and said efficient method reduces installation time to thereby reduce surgical team exposure to radiation, said method comprising:
- (a) using an image generating apparatus to accurately map a pedicle perimeter and a center point corresponding to said pedicle's axis, said image generating apparatus comprising a form of radiation emission;
- (b) placing a hemostatic pedicle punch on said mapped vertebrae pedicle, said hemostatic pedicle punch comprising a pedicle punch according to claim 14;
- (c) moving and positioning said hemostatic pedicle punch according to its image on said image generating apparatus until said axis of said pedicle punch has a trajectory path vector being as closely aligned with said axis of said vertebrae pedicle as possible, said close alignment being shown by said dot being concentric to said central point, and by said plurality of radiation opaque protrusions forming said bulls-eye to be concentric to said pedicle central point;
- (d) deploying said pedicle punch into said mapped vertebrae pedicle using an appropriate force, said force causing said generally flat surface of said shaft of said pedicle punch to be in direct contact with said mapped pedicle to effectively seal a cortical breach thereby created by said conical frustum of said cannula of said hemostatic pedicle punch, said sealing of said breach thereby imparting a hemostatic characteristic to said pedicle punch; said plurality of radiation opaque protrusions achieving shallow depth pedicle penetration and in combination with said base shaft serving to prevent toggling of said pedicle punch and maintain said sealing of said breach;
- (e) confirming proper placement of said hemostatic pedicle punch with said image generating apparatus;
- (f) insertion of a pedicle probe into said mapped pedicle through said cannula of said hemostatic pedicle punch to examine said mapped pedicle;
- (g) identification of a next pedicle requiring screw placement and performing said method according to steps (a) through (f) on said next pedicle until all of pedicle levels to be instrumented have one of said hemostatic pedicle punches installed therein;
- (h) removal of each of said hemostatic pedicle punches one by one by a surgeon, and use of said pedicle breach for a next step in said pedicle screw insertion process for said spinal implant.

21. A method of efficient vertebrae pedicle screw placement according to claim 20, wherein said image generating apparatus comprises a fluoroscope.

22. A method of efficient vertebrae pedicle screw placement according to claim 21, wherein said force is generated by a surgical mallet.

* * * * *